United States Patent [19]

Bright et al.

[11] Patent Number: 5,077,295

[45] Date of Patent: Dec. 31, 1991

[54] ANTIPSYCHOIC 4-(4-(3-BENZISOTHIAZOLYL)-1-PIPERAZINYL)BUYTL BRIDGED BICYCLE IMIDES

[75] Inventors: Gene M. Bright, Groton; John A. Love, III, Stonington, both of Conn.

[73] Assignee: Pfizer Inc., New York, N.Y.

[21] Appl. No.: 659,407

[22] PCT Filed: Sep. 16, 1988

[86] PCT No.: PCT/US88/03230

§ 371 Date: Mar. 8, 1991

§ 102(e) Date: Mar. 8, 1991

[51] Int. Cl.$^5$ .................. A61K 31/495; A61K 31/41; C07D 417/14

[52] U.S. Cl. ........................................ 514/254; 544/368

[58] Field of Search ........................... 544/368; 514/254

[56] References Cited

U.S. PATENT DOCUMENTS

| | | | |
|---|---|---|---|
| 3,717,634 | 2/1973 | Wu et al. | 260/256.4 |
| 3,907,801 | 9/1975 | Wu et al. | 260/268 |
| 4,411,901 | 10/1983 | Temple, Jr. et al. | 544/368 |
| 4,423,049 | 12/1983 | Temple | 424/251 |
| 4,452,799 | 6/1984 | Temple, Jr. et al. | 544/368 |
| 4,507,303 | 3/1985 | Ishizumi et al. | 514/255 |
| 4,543,355 | 9/1985 | Ishizumi et al. | 544/295 |
| 4,562,255 | 9/1985 | Freed et al. | 544/357 |
| 4,567,180 | 1/1986 | Hirose et al. | 514/253 |
| 4,590,196 | 5/1986 | Smith et al. | 544/368 |
| 4,656,173 | 4/1987 | Yevich et al. | 544/368 |
| 4,732,984 | 3/1988 | Abou-Gharbia et al. | 544/368 |
| 4,737,500 | 4/1988 | Sorg | 544/368 |
| 4,745,117 | 5/1988 | Ishizumi et al. | 544/368 |
| 4,748,240 | 5/1988 | Stack et al. | 544/47 |
| 4,883,795 | 11/1989 | Lowe et al. | 544/368 |

FOREIGN PATENT DOCUMENTS

| | | |
|---|---|---|
| 0196096 | 10/1986 | European Pat. Off. . |
| 3010760 | 1/1988 | Japan . |
| 8803024 | 5/1988 | PCT Int'l Appl. . |
| 2161807 | 1/1986 | United Kingdom . |

OTHER PUBLICATIONS

Bright et al., CA 113-13221g (1990).
Creese et al., Science 192, pp. 481-483 (1976).
Chemical Abstracts, vol. 92, 1980, Casten et al., Col. 1, Abstr. No. 92: 140722M.
Chemical Abstracts, vol. 106, 1987, Ishizumi et al., Col. 1, Abstr. No. 106: 33119f.

*Primary Examiner*—Cecilia Shen
*Attorney, Agent, or Firm*—Peter C. Richardson; J. Trevor Lumb; A. Dean Olson

[57] ABSTRACT

A series of bridged bicyclic imides having a 4-[4-(3-benzisothiazolyl)-1-piperazinyl]butyl group attached to the imide nitrogen are useful antipsychotic agents.

6 Claims, No Drawings

ANTIPSYCHOIC 4-(4-(3-BENZISOTHIAZOLYL)-1-PIPERAZINYL)-BUYTL BRIDGED BICYCLE IMIDES

BACKGROUND OF THE INVENTION

1. Field of the Invention

This invention relates to bridged bicyclic imides substituted on the nitrogen thereof with the 4-[4-(3-benzisothiazolyl)-1-piperazinyl]butyl group and their use as antipsychotics.

A variety of antipsychotic agents are known to date. These include tricyclic compounds such as chlorpromazine (2-chloro-N,N-dimethyl-10H-phenothiazine-10-propenamine); butyrophenone compounds such as haloperidol (4-[4-(4-chlorophenyl)-4-hydroxy-1-piperidinyl]-1-(4-fluorophenyl)-1-butanone); and certain spiroimide compounds such as busprione (8-[4-(2-pyrimidinyl)-1-piperazinylbutyl]-8-azaspiro[4,5]decane-7,9-dione) and tiaspirone (8-[4-(3-benzisothiazolyl)-1-piperazinyl butyl]-8-azaspiro[4,5]decane-7,9-dione). More recently, antipsychotics in which the azaspiro group is replaced by a fused bicyclic imide group and which allegedly exhibit fewer extra pyramidal side effects than previously described antipsychotics have been reported (see below). However, there remains a need for anti-psychotic agents which exhibit selectivity of action.

2. Description of the Prior Art

Certain glutarimide and succinimide compounds, substituted on nitrogen by a (4-aryl-1-piperazinyl)alkyl or (4-heteroaryl-1-piperazinyl)alkyl group, and having tranquillizing, antianxiety and/or anti-emetic properties are known from U.S. Pat. Nos. 3,717,634 and 3,907,801; 4,411,901 and 4,452,799; 4,182,763; 4,423,049; 4,507,303 and 4,543,355; 4,562,255; and EP-196,096. Korgaonka et al., J. Indian Chem. Soc., 60 874 (1983), disclose a number of N-(3-[4-aryl-1-piperazinyl]propyl) -camphorimides, which are alleged to have sedative properties in mice.

The most pertinent compounds of the above references have the general formula:

A—N⟨  ⟩N—(CH₂)₄—B wherein the values of A and B are: U.S. Pat. No. 3,717,634

$A = $ [pyrimidinyl structure] or [pyrimidinyl structure];

and
U.S. Pat. No. 3,907,901:

$B = -N$ [glutarimide-cyclohexane spiro structure] $(CH_2)_4$;

U.S. Pat. No. 4,182,673:

$A = $ [pyrimidinyl structure];

$B = -N$ [glutarimide-cyclopentane spiro structure];

U.S. Pat. No. 4,423,049:

$A = $ [pyrimidinyl structure];

$B = -N$ [glutarimide with dialkyl substitution] Alkyl, Alkyl;

U.S. Pat. No. 4,411,901

$A = $ [benzisothiazolyl structure];

and
U.S. Pat. No. 4,452,799:

$B = -N$ [spiro bicyclic imide structure];

U.S. Pat. No. 4,507,303

A = 2-pyrimidinyl;

and
U.S. Pat. No. 4,543,355;

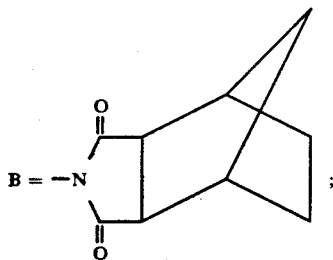

and
U.S. Pat. No. 4,567,755:
U.S. Pat. No. 4,745,117:

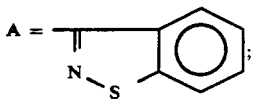

and
EP 0196096

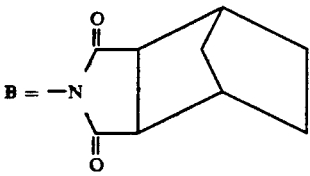

SUMMARY OF THE INVENTION

The compounds of this invention have the formula (I)

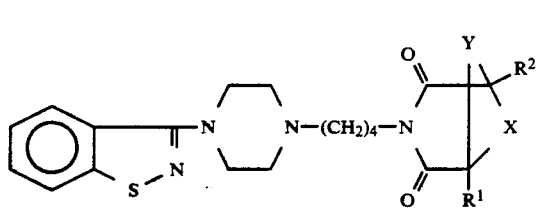

and the pharmaceutically-acceptable acid addition salts thereof, wherein

X is —$CH_2$—, —$CH_2CH_2$— or —$CH_2CH_2CH_2$—; and

Y is $CR^3R^4$ wherein each of $R^3$ and $R^4$, which may be alike or different, is hydrogen or methyl; and each of $R^1$ and $R^2$, which may be alike or different, is hydrogen, methyl or ethyl.

The present invention also relates to pharmaceutical compositions comprising a compound of formula (I) or a pharmaceutically-acceptable acid addition salt thereof and a pharmaceutically-acceptable carrier or diluent and to the use of formula (I) compounds or a pharmaceutical composition thereof for the treatment of a psychotic disorder in a human being suffering therefrom.

DETAILED DESCRIPTION OF THE INVENTION

The compounds of formula (I) are conveniently prepared by reacting N-(3-benzisothiazolyl)piperazine with a compound of formula (II)

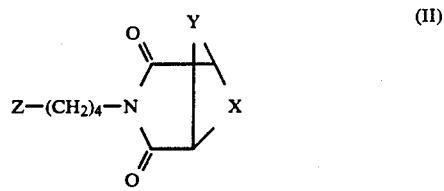

wherein Z is halo (especially chloro, bromo, iodo) or other readily displaced (leaving) group such as tosyloxy or mesyloxy. The reaction is carried out in a reaction-inert solvent (i.e., one in which at least one of the reactants is partially soluble and which does not adversely interact with reactants or product), generally at or near the reflux temperature of said solvent until substantially complete. The reaction temperature may range from 50° C. to about 200° C. In general, however, temperatures of from about 50° C. to 150° C. are adequate. The time required for substantially complete reaction is, of course, dependent upon the reaction temperature and the value of Z in the formula (II) reactant. A favored solvent, especially when Z in the formula (II) is tosyloxy is methyl isobutyl ketone. Other suitable, and typical, reaction-inert solvents are hydrocarbons such as benzene, toluene, xylene and decalin; the methyl and ethyl ethers of ethylene glycol, propylene glycol and diethylene glycol; and cyclic ethers such as tetrahydrofuran; acetonitrile.

The reaction is conducted in the presence of an inorganic or organic acid acceptor, representative of which are alkali and alkaline earth carbonates, bicarbonates or hydrides; or a tertiary amine. The preferred acid acceptors are sodium or potassium carbonate. Satisfactory yields of product are realized with reaction periods ranging from about 2-100 hours. The product is recovered by known methods such as extraction. Purification is accomplished by conventional methods such as chromatography on silica gel using chloroform/methanol or ethanol as eluant; or by crystallization techniques of the formula (I) compound or an acid addition salt thereof.

Other methods of preparing formula (I) compounds will be apparent to those skilled in the art.

The formula (II) reactants are prepared by reacting the appropriate anhydride, e.g., d-camphoric anhydride, with 4-hydroxybutylamine. This reaction is carried out by heating under substantially anhydrous conditions, substantially equimolar quantities of the two compounds at a temperature from 90° to 160° C., until the reaction is substantially complete. The two reactants are usually heated in a reaction-inert solvent; however, in those cases in which one or both of the reactants is molten at the reaction temperature, the two reactants can be heated in the absence of solvent. A reaction-inert solvent is one in which at least one of the reactants is soluble, and which does not adversely interact with either of the starting reactants or the product of the formula (I). Typical reaction-inert solvents which can be used include hydrocarbons such as benzene, toluene, xylene and decalin; the methyl and ethyl ethers of ethylene glycol, propylene glycol and diethylene glycol; and acetonitrile.

The product is recovered by standard procedures such as concentration of the reaction mixture.

The thus-obtained 4-hydroxybutyl substituted cyclic imide is then converted to a compound of formula (II). Preferred formula (II) compounds are those wherein Z is tosyloxy. Said compounds are obtained by reaction of the 4-hydroxybutyl substituted cyclic imide with an excess, e.g., 10%, of tosyl chloride in the presence of an acid acceptor, preferably sodium or potassium carbonate, in pyridine. The reaction is generally initially started at a temperature of about 0°–10° C. for one to two hours, after which it is allowed to rise to ambient temperature. Following a total reaction period of 4–6 hours, the tosyloxy derivative is recovered by extraction.

Acid-addition salts of a compound of the formula (I) are prepared by conventional methods. In a typical procedure, a compound of formula (I) is combined with a stoichiometric amount of an appropriate acid in an inert solvent, which can be aqueous, partially aqueous or non-aqueous. The salt is then recovered by solvent evaporation, by filtration if the salt precipitates spontaneously, or by precipitation using a non-solvent followed by filtration. Typical salts which can be prepared include sulfate, hydrochloride, hydrobromide, nitrate, phosphate, citrate, tartrate, pamoate, sulfosalicylate, methanesulfonate, benzenesulfonate and 4-toluenesulfonate salts.

The antipsychotic activity of compounds of formula (I) is demonstrated by various assay methods known to those skilled in the art. One of the more significant assays is the dopamine binding assay [Burt et al., *Molec. Pharmacol.* 12, 800 (1976); Creese et al., *Science* 192, 481 (1976)]. A further procedure of value in demonstrating their antipsychotic activity is the apomorphine stereotypy test [Janssen et al., *Arzneimittel Forsch.* 17, 841 (1966)]. Based upon these procedures, formula (I) compounds are found to exhibit potent inhibition of dopamine binding in the rat brain and to reverse apomorphine-induced stereotypy in rats.

A compound of formula (I), or a pharmaceutically-acceptable salt thereof, can be administered to a human subject either alone, or, preferably, in combination with pharmaceutically-acceptable carriers or diluents, in a pharmaceutical composition according to standard pharmaceutical practice. A compound can be administered orally or parenterally, which includes intravenous and intramuscular administration. However, the preferred route of administration is oral. Additionally, in a pharmaceutical composition comprising a compound of formula (I), or a pharmaceutically-acceptable salt thereof, the weight ratio of carrier to active ingredient will normally be in the range from 20:1 to 1:1, and preferably 10:1 to 1:1. However, in any given case, the ratio chosen will depend on such factors as the solubility of the active component, the dosage contemplated, and the precise dosage regimen.

For oral use of a compound of this invention, the compound can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular and intravenous use, sterile solutions of the active ingredient can be prepared, and the pH of the solutions should be suitably adjusted and buffered. For intravenous use, the total concentration of solutes should be controlled to render the preparation isotonic.

When a compound of the present invention is to be used in a human subject, the daily dosage will be determined by the prescribing physician. In general, the dosage will depend on the age, weight and response of the individual patient, as well as the severity of the patient's symptoms. However, in most instances, an effective amount of a compound of the formula (I), or a pharmaceutically-acceptable acid-addition salt thereof, will be from 1 to 300 mg per day, and preferably 5 to 100 mg per day, in single or divided doses. Naturally, the more active compounds of the invention will be used at the lower doses, while the less active compounds will be used at the higher doses.

The following examples and preparations are being provided solely for further illustration. For nuclear magnetic resonance spectra (NMR spectra), absorptions are given in parts per million (ppm) downfield from tetramethylsilane.

EXAMPLE 1

3-(4-[4-(3-Benzisothiazolyl)-1-piperazinyl]butyl)-1,8,8-trimethyl-3-azabicyclo[3.2.1]octane-2,4-dione

A.

3-(4-Hydroxybutyl)-1,8,8-trimethyl-3-azabicyclo[3.2.1]octane-2,4-dione

To a 125 ml round-bottomed flask equipped with Dean-Stark trap, condenser, and $N_2$ inlet were added 5.35 g (29 mmol) of d-camphoric anhydride, 2.49 g (28 mmol) of 4-hydroxybutylamine, and 60 ml of toluene. The reaction was refluxed with separation of water for 20 hours. It was then cooled, concentrated to an oil, and the oil dissolved in ethyl acetate. The ethyl acetate solution was washed with 5% HCl, 5% NaOH, and brine, dried over sodium sulfate, and evaporated to an oil, 6.0 g (85%).

NMR (delta, $CDCl_3$): 0.87 (two s, 6H), 1.11 (s, 3H), 1.3–1.5 (m, 2H), 1.65–1.95 (m, 2H), 2.54 (s, 1H), 3.3–3.7 (m, 4H).

MS (%): 254 (18), 253 (18, parent), 236 (23), 235 (37), 226 (17), 223 (47), 222 (23), 220 (21), 209 (13), 208 (14), 206 (29), 195 (33), 194 (100), 182 (76), 181 (22), 166 (24), 138 (31), 137 (31), 136 (15), 124 (17), 123 (18), 112 (35), 111 (15), 110 (28), 109 (86), 108 (10), 105 (12), 98 (27), 97 (12), 96 (34), 95 (55), 93 (11), 91 (14).

B 3-(4-Tosyloxybutyl)-1,8,8-trimethyl-3-azabicyclo[3.2.1]octane-2,4-dione

To a 250 ml round-bottomed flask equipped with $N_2$ inlet were added 5.35 g (21.1 mmol) of 3-(4-hydroxybutyl-1,8,8-trimethyl-3-azabicyclo[3.2.1]octane-2,4-dione, 4.43 g (23.3 mmol) of tosyl chloride, 5.84 g (42.2 mmol) of potassium carbonate, and 70 ml of pyridine. The reaction was initially stirred at 0° C., then stirred at room temperature for 5 hours. It was then poured into water and extracted into methylene chloride. The organic layer was subsequently washed with water, copper sulfate solution, sodium carbonate solution, water, and brine, dried over sodium sulfate, and evaporated to an oil, 5.3 g (62%).

NMR (delta, CDCl$_3$): 0.87 (two s, 6H), 1.11 (s, 3H), 1.3–1.5 (m, 2H), 1.65–1.95 (m, 2H), 2.42 (s, 3H), 3.5–3.7 (m, 2H), 3.9–4.1 (m, 2H), 7.2–7.8 (m, 4H).

MS (%): 409 (10), 408 (31), 407 (11, parent), 252 (21), 237 (24), 236 (100), 235 (88), 226 (10), 220 (20), 207 (44), 206 (81), 194 (40), 182 (12), 173 (10), 166 (14), 155 (20), 138 (11), 137 (14), 136 (11), 112 (11), 110 (13), 109 (49), 108 (12), 107 (11), 96 (14), 95 (37), 93 (12), 91 (81).

C.
3-(4-[4-(3-Benzisothiazolyl)-1-piperazinyl]butyl)-1,8,8-trimethyl-3-azabicyclo-[3.2.1]octane-2,4-dione Hydrochloride To a 125 ml round-bottomed flask equipped with condenser and N$_2$ inlet were added 0.5 g (1.95 mmol) of N-(3-benzisothiazolyl)-piperazine (prepared according to U.S. Pat. No. 4,452,799), 0.8 g (1.95 mmol) of 3-(4-tosyloxybutyl)-1,8,8-trimethyl-3-azabicyclo[3.2.1]-octane-2,4-dione, 0.42 g (3.91 mmol) of sodium carbonate, and 50 ml of methylisobutylketone. The reaction was refluxed 4 days, cooled, and evaporated. The oil was taken up in ethyl acetate, washed with water and brine, dried over sodium sulfate, and evaporated to an oil. The oil was dissolved in ether, treated with ether saturated with HCl, and the precipitate collected under N$_2$ and dried to a hygroscopic, tan solid, 210 mg (22%).

NMR (delta, DMSO-d$_6$): 0.88 (s, 3H), 0.92 (s, 3H), 1.11 (s, 3H), 1.4–1.5 (m, 2H), 1.6–1.8 (m, 2H), 1.8–2.0 (m, 2H), 2.1–2.3 (m, 1H), 2.7 (m, 1H), 3.1–3.7 (m, 10H), 4.0–4.1 (m, 2H), 7.4–7.7 (m, 2H), 8.1–8.2 (m, 2H). IR (cm$^{-1}$, DMSO): 1724 and 1664 (C=O).

MS (%): 454 (20), 439 (10), 319 (13), 318 (46), 305 (11), 304 (20), 292 (16), 291 (62), 280 (13), 279 (64), 277 (12), 236 (16), 232 (55), 203 (16), 194 (11), 190 (12), 189 (16), 179 (11), 178 (11), 177 (65), 176 (44), 175 (13), 166 (12), 164 (13), 163 (74), 162 (15), 151 (23), 150 (15), 149 (17), 137 (30), 136 (22), 135 (69), 134 (24), 125 (20), 124 (19), 123 (96), 120 (15), 112 (19), 111 (64), 110 (36), 109 (100), 108 (20), 107 (11), 105 (11).

EXAMPLE 2

In like manner the following compounds of formula (I) are prepared according to the procedure of Example 1 but using the appropriate bicyclic anhydride in place of d-camphoric anhydride:

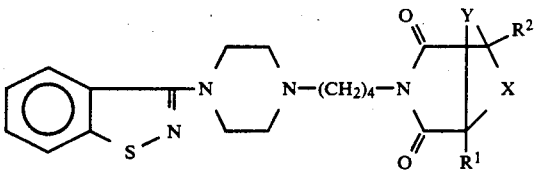

| R$^1$ | R$^2$ | X | Y |
| --- | --- | --- | --- |
| H | H | CH$_2$ | CH$_2$ |
| H | H | (CH$_2$)$_2$ | CH$_2$ |
| H | H | (CH$_2$)$_3$ | CH$_2$ |
| H | H | (CH$_2$)$_2$ | (CH$_2$)$_2$ |
| H | H | CH$_2$ | C(CH$_3$)$_2$ |
| H | H | (CH$_2$)$_2$ | C(CH$_3$)$_2$ |
| CH$_3$ | CH$_3$ | (CH$_2$)$_2$ | CH$_2$ |
| CH$_3$ | CH$_2$CH$_3$ | (CH$_2$)$_2$ | CH$_2$ |

We claim:
1. A compound of the formula (I)

or a pharmaceutically-acceptable acid addition salt thereof, wherein
each of R$^1$ and R$^2$, which may be alike or different, is hydrogen, methyl or ethyl;
X is —CH$_2$—, —CH$_2$CH$_2$— or —CH$_2$CH$_2$CH$_2$—; and
Y is (CH$_2$)$_2$ - or CR$^3$R$^4$ wherein each of R$^3$ and R$^4$, which may be alike or different, is hydrogen or methyl.

2. A compound according to claim 1 wherein each of R$^1$ and R$^2$ is hydrogen; Y is CH$_2$ and X is —CH$_2$—.

3. A compound according to claim 1 wherein R$^1$ is methyl; R$^2$ is hydrogen; Y is CH$_2$; and X is CH$_2$CH$_2$—.

4. The compound according to claim 1 wherein R$^1$ is methyl; R$^2$ is hydrogen; Y is C(CH$_3$)$_2$ and X is —CH$_2$CH$_2$—.

5. A method of treating psychosis in a subject in need of such treatment which comprises administering to said subject an antipsychotic effective amount of a compound according to claim 1.

6. A pharmaceutical composition having antipsychotic activity comprising an antipsychotic effective amount of a compound according to claim 1, and a pharmaceutically-acceptable carrier.

* * * * *